Aug. 14, 1962 R. A. CALLISON Plant Pat. 2,166

PEACH TREE

Filed Oct. 10, 1961

WITNESS

Addison E Avery

INVENTOR

Robert A. Callison

Webster & Webster

ATTYS.

United States Patent Office

Plant Pat. 2,166
Patented Aug. 14, 1962

2,166
PEACH TREE

Robert A. Callison, 6808 Ave. 404, Dinuba, Calif.

Filed Oct. 10, 1961, Ser. No. 144,275
1 Claim. (Cl. 47—62)

This invention relates to a new and distinct variety of hardy, vigorous, productive peach tree which bears uniformly large and symmetrical fruit having yellow skin overspread to a substantial extent with a bright red blush, and yellow flesh without red fibers.

The present variety, with respect to the fruit, ripens during the same season and most nearly resembles the Redtop peach (F–15) heretofore introduced by the United States Department of Agriculture Station at Fresno, California, but is characteristically distinguished by a brighter exterior color, and flesh which ripens evenly and has a sub-acid distinctly delicate flavor, as is most desirable in a dessert peach.

The fruit of the present variety is additionally characterized by skin which has no astringent flavor; the skin being tenacious to the flesh when the fruit is hard-ripe but frees when soft-ripe. Further, the fruit has good storage and excellent shipping qualities, and when picked hard-ripe has an excellent shelf life and continues to ripen.

The present variety of peach tree was originated by me as a cross using as male pollen a nectarine mutation on a Blazing Gold peach tree, on a J. H. Hale peach tree as the female. From such a cross a substantial number of seedlings were grown in an experimental plot in my orchard located near Dinuba, Tulare County, California.

The variety as herein claimed was selected from such seedlings after careful observation and the determination of its novel and commercially advantageous characteristics.

Subsequent to origination of the variety I asexually reproduced it in my orchard, located as aforesaid, by budding on mature orchard trees; such reproductions—in maturity—having been found to run true to the parent seedling in all respects.

Figure 1:
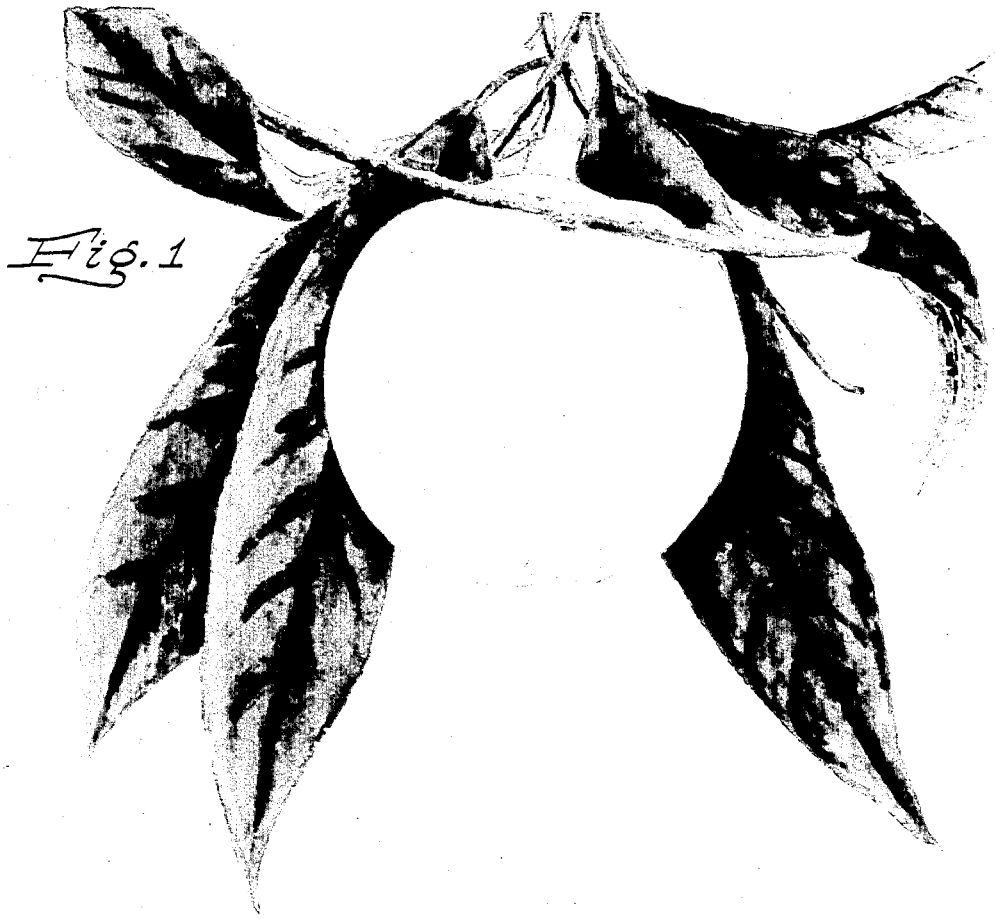
FIG. 1 is an elevation showing one of the peaches, together with a twig and leaves.
Figure 2:
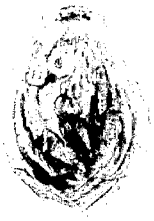
FIG. 2 is a sectional elevation of one of the peaches with the stone remaining in place.

Referring now more specifically to the promological details of this new and distinct variety of peach tree, the following is an outline description thereof; all major color plate identifications being by reference to Maerz and Paul Dictionary of Color, except where common terms of color definition are employed:

Tree:
- *Size.*—Large.
- *Vigor.*—Vigorous.
- *Growth.*—Good spreading habits.
- *Density.*—Quite dense with foliage.
- *Shape.*—Develops a vase shaped upper scaffold.
- *Hardiness.*—Hardy.
- *Production.*—Productive.
- *Bearing.*—Consistently a good bearer, both after mild and cold winters.

Trunk:
- *Size.*—Stocky; well proportioned.
- *Surface.*—Medium checking on the exterior bark.

Branches:
- *Size.*—Medium.
- *Surface.*—Medium checking on the exterior bark.
- *Color.*—Dull brown-grey.
- *Lenticels.*—Number—few. Size—small to medium.

Leaves:
- *Size.*—Large. Average length—6¼″. Average width—1⅝″.
- *Form.*—Lanceolate.
- *Thickness.*—Medium.
- *Texture.*—Medium.
- *Surface.*—Smooth.
- *Margin.*—Evenly crenate along the entire margin.
- *Petiole.*—Medium length, averaging ⅜″ to ⅝″. Thick, with uniform broad groove.
- *Glands.*—Average number—four. Alternate; small; reniform. Green, with pale yellow rim. Positioned on the average two on the petiole and two on the base of the leaf approximately ⅛″ from the petiole.
- *Stipulses.*—None.
- *Color.*—Top side—medium green (22–L–8). Under side—lighter green (22–J–6).

Flower buds:
- *Hardiness.*—Hardy, no indication of bud drop. Dormancy requirement estimated at near the 900 hour group.
- *Size.*—Large.
- *Length.*—Medium to long.
- *Form.*—Obtuse. Well filled but slightly rounded at the apex. Appressed to the twig with no pubescence.

Flowers:
- *Blooming period.*—Average date of first bloom—March 5th. Average date of last bloom—March 8th. Average as compared with other varieties.
- *Size.*—Medium.
- *Color.*—Pink.

Fruit:
- *Maturity when described.*—Hard-ripe, edible and at maturity for shipment to local markets—June 27, 1961.
- *Date of first picking.*—June 25, 1961.
- *Date of last picking.*—July 4, 1961.
- *Comparative harvest.*—As compared with other varieties, harvest is in generally the same season as the Early Elberta, Red Globe, Merrill Hale, and Redtop.
- *Size.*—Uniformly large. Average diameter axially—3¼″. Average transversely in suture plane—3¼″.
- *Form.*—Uniformly symmetrical in all dimensions. Very well rounded over the entire suture area.
- *Suture.*—A distinct line extending from the base to the pistil point.
- *Ventral surface.*—Well rounded. Broad at the base, with both lips equal.
- *Cavity.*—Flaring. Slightly elongated in the suture plane, with the suture showing. Average depth—7/16″. Average breadth—⅝″. Average length—¾″.
- *Base.*—Evenly rounded on all surfaces.
- *Apex.*—Well rounded, with a slight depression opposite the suture line.
- *Pistil point.*—Does not extend beyond the apex.

Skin:
- *Thickness.*—Medium.
- *Texture.*—Medium, with no astringent flavor.
- *Tenacity.*—Tenacious to flesh when fruit hard-ripe, but free when soft-ripe.
- *Tendency to crack.*—None.
- *Down.*—Moderate; rolls when hand rubbed.
- *Color.*—Yellow ground or base color (9–L–2), overspread or overlaid with a bright red blush (3–L–10 to 4–L–6) on about two-thirds of the surface.

Flesh:

*Amygdalin.*—Scant.

*Juice.*—Moderate; distinctly rich in flavor.

*Texture.*—Medium firm; melting.

*Fibers.*—Few; fine; tender.

*Ripens.*—Evenly throughout.

*Flavor.*—Sub-acid; distinctly delicate.

*Aroma.*—Pronounced; pleasant; distinct peach aroma.

*Eating quality.*—Excellent dessert qualities, especially as to flavor.

*Color.*—Yellow (9–I–6 to 9–L–7), without red fibers; the flesh next to the pit cavity being pale pink with a few pink fibers extending into the flesh. Surface of pit cavity pale pink, with pink fibers extending into the pit, becoming pale yellow.

Stone:

*Type.*—Free. Retains short fibers along the ventral edges and along the ridges.

*Size.*—Medium. Average length—1⅝″. Average breadth—1¼″. Average thickness—⅞″.

*Form.*—Oblong; sharply pointed on the apex; cuneate toward the base.

*Hilum.*—Oblong; narrow; slightly indented; serrated edges.

*Apex.*—Acuminate; sharp point.

*Sides.*—Unequal. Rounded on the left side and flatted on the right side.

*Surface.*—Irregularly furrowed and pitted. Pitted near the hilum and deep furrows near the apex.

*Ridges.*—Both sides; jagged; interrupted; extend from base to apex.

*Pits.*—Elongated; uniform.

*Ventral edge.*—Thin, with wing toward base.

*Dorsal edge.*—Narrow, with shallow groove throughout.

*Tendency to split.*—None.

*Color.*—Reddish purple (53–L–1), partially marked with brown (7–E–10).

Use: Market; dessert; shipping.

Keeping quality: Pressure tests indicate good storage qualities. Fruit picked hard-ripe has excellent shelf life and continues to ripen.

Shipping quality: Excellent.

The existing varieties mentioned herein are unpatented except Blazing Gold, United States Plant Patent No. 1,127, and Merrill Hale, United States Plant Patent No. 1,246.

The tree and its fruit herein described may vary in slight detail due to climatic and soil conditions under which the variety may be grown; the present description being of the variety as grown near Dinuba, California.

The following is claimed:

A new and distinct variety of peach tree, as illustrated and described, which is hardy, vigorous, and productive, the tree being a consistently good bearer, both after mild and cold winters, of uniformly large and symmetrical freestone fruit having yellow skin overspread to a substantial extent with a bright red blush, and yellow flesh without red fibers; the variety being characterized—in comparison to the Redtop peach—by generally the same harvest season but having a brighter exterior color; and further characterized by sub-acid, distinctly delicately flavored, fruit having medium firm and melting flesh which ripens evenly and skin which has no astringent flavor, the skin being tenacious to the flesh when the fruit is hard-ripe but frees when soft-ripe.

No references cited.